(12) United States Patent
Kim et al.

(10) Patent No.: US 11,484,415 B2
(45) Date of Patent: Nov. 1, 2022

(54) CAGE HAVING SPIKE

(71) Applicant: LDR Medical, S.A.S., Sainte-Savine (FR)

(72) Inventors: Seo-Kon Kim, Gyeonggi-do (KR); Il Kim, Seoul (KR)

(73) Assignee: LDR Medical S.A.S.

( * ) Notice: Subject to any disclaimer, the term of this patent is extended or adjusted under 35 U.S.C. 154(b) by 159 days.

(21) Appl. No.: 16/987,843

(22) Filed: Aug. 7, 2020

(65) Prior Publication Data

US 2020/0360152 A1 Nov. 19, 2020

Related U.S. Application Data

(60) Continuation of application No. 15/723,174, filed on Oct. 3, 2017, now Pat. No. 10,765,531, which is a (Continued)

(30) Foreign Application Priority Data

Sep. 11, 2013 (KR) .................. 10-2013-0108840

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/305* (2013.01);
(Continued)

(58) Field of Classification Search
CPC .. A61F 2002/30373; A61F 2002/30433; A61F 2002/30481; A61F 2002/30484;
(Continued)

(56) References Cited

U.S. PATENT DOCUMENTS 6,447,546 B1  9/2002  Bramlet et al.
8,221,422 B2  7/2012  Mangione
(Continued)

FOREIGN PATENT DOCUMENTS

CA   2853305 A1   5/2013
CN   201244104 Y  5/2009
(Continued)

OTHER PUBLICATIONS

"U.S. Appl. No. 14/460,536, Corrected Notice of Allowance dated Jun. 1, 2017", 9 pgs.
(Continued)

*Primary Examiner* — Samuel S Hanna
(74) *Attorney, Agent, or Firm* — Sheridan Ross P.C.

(57) ABSTRACT

Disclosed is a cage which is inserted between vertebral bodies of a cervical vertebra or spine during an operation for treating a cervical disc disease, myelosis, or fracture of the cervical vertebra or spine, and more particularly, to a cage with spikes, including upper and lower spikes which are attached to a clip inserted into a main body of the cage, unfolded upward and downward from the main body, and locked to vertebral bodies of a cervical vertebra or spine positioned at the top and bottom of the cage such that the cage is fixed and locked between the vertebral bodies.

19 Claims, 21 Drawing Sheets

Related U.S. Application Data division of application No. 14/460,536, filed on Aug. 15, 2014, now Pat. No. 9,775,722.

(52) U.S. Cl.
CPC ............... *A61F 2002/30373* (2013.01); *A61F 2002/30433* (2013.01); *A61F 2002/30481* (2013.01); *A61F 2002/30484* (2013.01); *A61F 2002/30492* (2013.01); *A61F 2002/30579* (2013.01); *A61F 2002/30593* (2013.01); *A61F 2002/30624* (2013.01); *A61F 2002/30822* (2013.01); *A61F 2002/30892* (2013.01); *A61F 2002/30904* (2013.01); *A61F 2310/00017* (2013.01); *A61F 2310/00023* (2013.01); *A61F 2310/00029* (2013.01); *A61F 2310/00089* (2013.01); *A61F 2310/00095* (2013.01); *A61F 2310/00131* (2013.01); *A61F 2310/00239* (2013.01)

(58) Field of Classification Search
CPC ...... A61F 2002/30492; A61F 2002/305; A61F 2002/30579; A61F 2002/30624; A61F 2/447; A61F 2/4611; A61F 2002/30593; A61F 2002/30822; A61F 2002/30892; A61F 2002/30904

See application file for complete search history.

(56) References Cited

U.S. PATENT DOCUMENTS

| | | | |
|---|---|---|---|
| 9,566,164 B2 | 2/2017 | Zeegers | |
| 9,763,803 B2 | 9/2017 | Dinville et al. | |
| 9,775,722 B2 | 10/2017 | Kim et al. | |
| 2003/0195626 A1 | 10/2003 | Huppert | |
| 2004/0172020 A1 | 9/2004 | Beaurain et al. | |
| 2004/0199254 A1 | 10/2004 | Louis et al. | |
| 2004/0243240 A1 | 12/2004 | Beaurain et al. | |
| 2004/0254577 A1 | 12/2004 | Delecrin et al. | |
| 2005/0010215 A1 | 1/2005 | Delecrin et al. | |
| 2005/0065611 A1 | 3/2005 | Huppert et al. | |
| 2005/0107788 A1 | 5/2005 | Beaurain et al. | |
| 2005/0197706 A1 | 9/2005 | Hovorka et al. | |
| 2005/0246024 A1 | 11/2005 | Zeegers | |
| 2006/0155377 A1 | 7/2006 | Beaurain et al. | |
| 2006/0173544 A1 | 8/2006 | Gau | |
| 2006/0282074 A1 | 12/2006 | Renaud et al. | |
| 2007/0016217 A1 | 1/2007 | Dinville | |
| 2007/0073404 A1 | 3/2007 | Rashbaum et al. | |
| 2007/0162130 A1 | 7/2007 | Rashbaum et al. | |
| 2007/0270951 A1 | 11/2007 | Davis et al. | |
| 2008/0021562 A1 | 1/2008 | Huppert | |
| 2008/0200984 A1 | 8/2008 | Jodaitis et al. | |
| 2008/0234686 A1 | 9/2008 | Beaurain et al. | |
| 2008/0255617 A1 | 10/2008 | Cho et al. | |
| 2008/0312743 A1 | 12/2008 | Villa et al. | |
| 2009/0099604 A1 | 4/2009 | Cho et al. | |
| 2009/0105832 A1 | 4/2009 | Allain et al. | |
| 2009/0132054 A1 | 5/2009 | Zeegers | |
| 2009/0157188 A1 | 6/2009 | Zeegers | |
| 2009/0182381 A1 | 7/2009 | Beaurain et al. | |
| 2009/0204219 A1 | 8/2009 | Beaurain et al. | |
| 2009/0216241 A1 | 8/2009 | Dinville | |
| 2009/0222092 A1 | 9/2009 | Davis et al. | |
| 2009/0270990 A1 | 10/2009 | Louis et al. | |
| 2010/0087925 A1 | 4/2010 | Kostuik et al. | |
| 2010/0204739 A1 | 8/2010 | Bae et al. | |
| 2010/0280618 A1 | 11/2010 | Jodaitis et al. | |
| 2011/0077739 A1 | 3/2011 | Rashbaum et al. | |
| 2011/0178599 A1 | 7/2011 | Brett | |
| 2011/0230971 A1 | 9/2011 | Donner et al. | |
| 2012/0053693 A1 | 3/2012 | Zeegers | |
| 2012/0078373 A1 | 3/2012 | Gamache et al. | |
| 2012/0116466 A1 | 5/2012 | Dinville et al. | |
| 2012/0191196 A1 | 7/2012 | Louis et al. | |
| 2012/0265248 A1 | 10/2012 | Delecrin et al. | |
| 2012/0310356 A1 | 12/2012 | Davis et al. | |
| 2012/0330424 A1 | 12/2012 | Zeegers | |
| 2013/0013006 A1 | 1/2013 | Rashbaum et al. | |
| 2013/0041408 A1* | 2/2013 | Dinville | A61B 17/7071 606/249 |
| 2013/0110242 A1 | 5/2013 | Kirwan et al. | |
| 2013/0150968 A1 | 6/2013 | Dinville et al. | |
| 2013/0166029 A1 | 6/2013 | Dinville et al. | |
| 2013/0226300 A1 | 8/2013 | Chataigner et al. | |
| 2013/0253648 A1 | 9/2013 | Beaurain et al. | |
| 2013/0253651 A1 | 9/2013 | Dinville | |
| 2013/0282124 A1 | 10/2013 | Jodaitis et al. | |
| 2014/0052262 A1 | 2/2014 | Brett | |
| 2014/0114413 A1 | 4/2014 | Allain et al. | |
| 2014/0121778 A1 | 5/2014 | Huppert | |
| 2014/0135932 A1 | 5/2014 | Davis et al. | |
| 2014/0135935 A1 | 5/2014 | Vila et al. | |
| 2014/0148855 A1 | 5/2014 | Beaurain et al. | |
| 2014/0214168 A1 | 7/2014 | Jodaitis | |
| 2014/0228885 A1 | 8/2014 | Dinville et al. | |
| 2014/0316466 A1 | 10/2014 | Dinville et al. | |
| 2014/0364949 A1 | 12/2014 | Beaurain et al. | |
| 2015/0025638 A1 | 1/2015 | Rashbaum et al. | |
| 2015/0032209 A1 | 1/2015 | Hovorka et al. | |
| 2015/0045893 A1 | 2/2015 | Dinville et al. | |
| 2015/0051702 A1 | 2/2015 | Chataigner et al. | |
| 2015/0080959 A1 | 3/2015 | Renaud et al. | |
| 2015/0127107 A1 | 5/2015 | Kim et al. | |
| 2015/0127109 A1 | 5/2015 | Brett | |
| 2015/0182259 A1 | 7/2015 | Cho et al. | |
| 2015/0182264 A1 | 7/2015 | Delecrin et al. | |
| 2015/0190240 A1 | 7/2015 | Rashbaum et al. | |
| 2015/0209089 A1 | 7/2015 | Chataigner et al. | |
| 2015/0245918 A1 | 9/2015 | Zeegers | |
| 2015/0250605 A1 | 9/2015 | Chataigner et al. | |
| 2015/0257895 A1 | 9/2015 | Zeegers | |
| 2015/0320568 A1 | 11/2015 | Ameil et al. | |
| 2016/0008142 A1 | 1/2016 | Louis et al. | |
| 2016/0051380 A1 | 2/2016 | Dinville et al. | |
| 2016/0100870 A1 | 4/2016 | Lavigne et al. | |
| 2016/0100953 A1 | 4/2016 | Dinville et al. | |
| 2016/0166402 A1 | 6/2016 | Steib | |
| 2016/0220389 A1 | 8/2016 | Dinville | |
| 2016/0235547 A1 | 8/2016 | Beaurain et al. | |
| 2016/0317190 A1 | 11/2016 | Beaurain et al. | |
| 2016/0317195 A1 | 11/2016 | Dinville et al. | |
| 2016/0324655 A1 | 11/2016 | Beaurain et al. | |
| 2017/0027620 A1 | 2/2017 | Dinville et al. | |
| 2017/0042692 A1 | 2/2017 | Stewart et al. | |
| 2017/0056198 A1 | 3/2017 | Ameil et al. | |
| 2017/0071754 A1 | 3/2017 | Zeegers | |
| 2017/0095350 A1 | 4/2017 | Brett | |
| 2017/0112636 A1 | 4/2017 | Jodaitis et al. | |
| 2017/0172761 A1 | 6/2017 | Vila et al. | |
| 2017/0196596 A1 | 7/2017 | Delecrin et al. | |
| 2017/0209181 A1 | 7/2017 | Beaurain et al. | |
| 2017/0216048 A1 | 8/2017 | Zeegers | |
| 2017/0224393 A1 | 8/2017 | Lavigne et al. | |
| 2017/0246007 A1 | 8/2017 | Chataigner et al. | |
| 2017/0246008 A1 | 8/2017 | Mercier et al. | |
| 2017/0252179 A1 | 9/2017 | Rashbaum et al. | |
| 2017/0252183 A1 | 9/2017 | Davis et al. | |
| 2017/0299525 A1 | 10/2017 | Cui et al. | |
| 2017/0311997 A1 | 11/2017 | Lequette et al. | |
| 2018/0104069 A1 | 4/2018 | Kim et al. | |

FOREIGN PATENT DOCUMENTS

| | | |
|---|---|---|
| CN | 101878007 A | 11/2010 |
| CN | 101917937 A | 12/2010 |
| CN | 102458278 A | 5/2012 |
| CN | 103251465 A | 8/2013 |
| KR | 10-0900991 | 6/2009 |
| KR | 10-2011-0011049 | 2/2011 |
| KR | 10-2011-0033707 | 3/2011 |
| WO | WO-0213732 A2 | 2/2002 |
| WO | WO-2010028045 A1 | 3/2010 |

(56) References Cited

FOREIGN PATENT DOCUMENTS

| WO | WO-2010092893 A1 | 8/2010 |
|---|---|---|
| WO | WO-2011008864 A1 | 1/2011 |
| WO | WO-2012078657 A2 | 6/2012 |
| WO | WO-2012129206 A2 | 9/2012 |
| WO | WO-2013062716 A1 | 5/2013 |

OTHER PUBLICATIONS

"U.S. Appl. No. 14/460,536, Notice of Allowance dated May 12, 2017", 13 pgs.
"U.S. Appl. No. 14/460,536, Preliminary Amendment filed Jan. 22, 2015", 29 pgs.
"U.S. Appl. No. 14/460,536, Response filed Mar. 20, 2017 to Restriction Requirement dated Jan. 20, 2017", 9 pgs.
"U.S. Appl. No. 14/460,536, Restriction Requirement dated Jan. 20, 2017", 6 pgs.
"U.S. Appl. No. 15/723,174, Non Final Office Action dated Jan. 27, 2020", 12 pgs.
"U.S. Appl. No. 15/723,174, Notice of Allowance dated May 6, 2020", 9 pgs.
"U.S. Appl. No. 15/723,174, Response filed Apr. 27, 2020 to Non Final Office Action dated Jan. 27, 2020", 9 pgs.
"U.S. Appl. No. 15/723,174, Response filed Dec. 17, 2019 to Restriction Requirment dated Oct. 24, 2019", 8 pgs.
"U.S. Appl. No. 15/723,174, Restriction Requirement dated Oct. 24, 2019", 6 pgs.
"Chinese Application Office Action dated Dec. 8, 2015".
"Japanese Application Office Action dated May 11, 2015".
"Korean Application Amendment filed Apr. 16, 2015", Solco Biomedical.
"Korean Application Office Action dated Feb. 16, 2015".
U.S. Appl. No. 14/460,536 U.S. Pat. No. 9,775,722, filed Aug. 15, 2014, Cage Having Spike.
U.S. Appl. No. 15/723,174, filed Oct. 3, 2017, Cage Having Spike.

\* cited by examiner

CAGE HAVING SPIKE

CROSS-REFERENCE TO RELATED APPLICATIONS

This application is a continuation of U.S. patent application Ser. No. 15/723,174, filed Oct. 3, 2017, which is a divisional of U.S. patent application Ser. No. 14/460,536 filed Aug. 15, 2014, and issuing as U.S. Pat. No. 9,775,722 on Oct. 3, 2017, which claims the benefit of Korean Patent Application No. 10-2013-108840, filed on Sep. 11, 2013, in the Korean Intellectual Property Office, all of which are incorporated herein by reference in their entirety.

BACKGROUND OF THE INVENTION

1. Field of the Invention

The present invention relates to a cage which is inserted between vertebral bodies of a cervical vertebra or spine during an operation for treating a cervical disc disease, myelosis, or fracture of the cervical vertebra or spine, and more particularly, to a cage including upper and lower spikes which are attached to a clip inserted into a main body of the cage, unfolded to protrude from the top and bottom of the main body, and locked to vertebral bodies of a cervical vertebra or spine positioned at the top and bottom of the cage such that the cage is fixed between the vertebral bodies.

2. Description of Related Art

In general, an operation of inserting an artificial compensation-chain cage between vertebral bodies of a cervical vertebra or spine is performed in order to treat a cervical disc disease, myelosis, or fracture of a cervical vertebra or spine in the orthopedics department or neurosurgery department. More specifically, an operator removes a cervical disc of a diseased part so as to eliminate compression of nerve, and inserts the artificial compensation-cage to recover and maintain the interval of the part from which the cervical disc has been removed.

Such a cage is likely to be moved within the intervertebral space by stress applied when the patient moves. Thus, an additional unit must be provided to prevent the pivot of the cage while preventing the movement of the cervical vertebra or spine within the intervertebral space.

According to Korean Patent Laid-open Publication No. 10-2011-33707 which has disclosed a cervical vertebral body fusion device, Korean Patent No. 900991 which has disclosed a cage for spinal implant, and Korean Patent Laid-open Publication No. 10-2011-11049 which has disclosed a fusion cage between vertebral bodies, a cage is inserted into a part from which an intervertebral disc has been removed, and a reinforcement plate having a predetermined length is fixed to a cervical vertebra or spine through a screw, thereby preventing the displacement of the inserted cage.

In the above-described techniques, however, the reinforcement plate is fixed at the front of the cage through the screw. Thus, the head of the screw inserted into the plate or a part of the plate may protrude more than protruding parts of the cervical vertebra or spine, which are positioned at the top and bottom of the part from which the intervertebral disk has been removed and in which the cage is installed. In this case, according to a force applied when a patient moves with time, the cage may be moved or pivoted within the intervertebral space such that the protruding head of the screw within the intervertebral space comes in contact with blood tissues or nerve tissues passing through the cervical vertebra or spine. Thus, there is a demand for the development of a more stable cage.

Furthermore, the plate and the screw are used to fix the cage. In this case, it is extremely difficult to fix the plate through the screw in such a small intervertebral space, while much attention is needed. Thus, special technical skills are required for an operator.

SUMMARY OF THE INVENTION

Accordingly, the present invention has been made to solve the above-mentioned problems involved in the prior art, and it is an object of the present invention to provide a cage with spikes which is capable of preventing the occurrence of a protruding part of a screw so as to minimize interference with blood tissues or nerve tissues passing through the cervical vertebra or spine when the cage is placed, and performing a procedure for fixing the cage in a relatively easy and simple manner, thereby improving the stability of operation.

To accomplish the above object, the present invention provides a cage with spikes which includes upper and lower spikes which are attached to a clip inserted into a main body of the cage, unfolded upward and downward from the main body, and locked to vertebral bodies of a cervical vertebra or spine positioned at the top and bottom of the cage such that the cage is fixed and locked between the vertebral bodies.

The cage in accordance with the embodiment of the present invention has the following effects.

First, the cage is locked and fixed between the vertebral bodies of a cervical vertebra or spine at the part from which an intervertebral disk has been removed, by the spikes unfolded upward and downward from the main body of the cage. Thus, it is possible to significantly reduce the possibility that the screw for fixing the cage or a part of the plate will interfere with the nerve tissue or blood tissue passing through the cervical vertebra or spine at the part from which the intervertebral disk was removed and in which the cage is installed. Furthermore, prognosis of a patient having received an intervertebral disk surgery may be improved.

Furthermore, the cage in accordance with the embodiment of the present does not employ a plate or screw unlike the conventional cages, but includes the spikes. Thus, it is possible to omit a complicated operation of fixing a plate through a screw in a small intervertebral space in the related art. Therefore, the convenience of the procedure may be improved, and the operation process may be simplified to provide the stability of the operation.

BRIEF DESCRIPTION OF THE DRAWINGS

The above and other objects, features and advantages of the present invention will be apparent from the following detailed description of the preferred exemplary embodiments of the invention in conjunction with the accompanying drawings, in which:

FIGS. 1A to 11C are detailed diagrams of a guide block of the cage in accordance with the embodiment of the present invention;

EXPLANATION ON SYMBOLS

Figure 1:
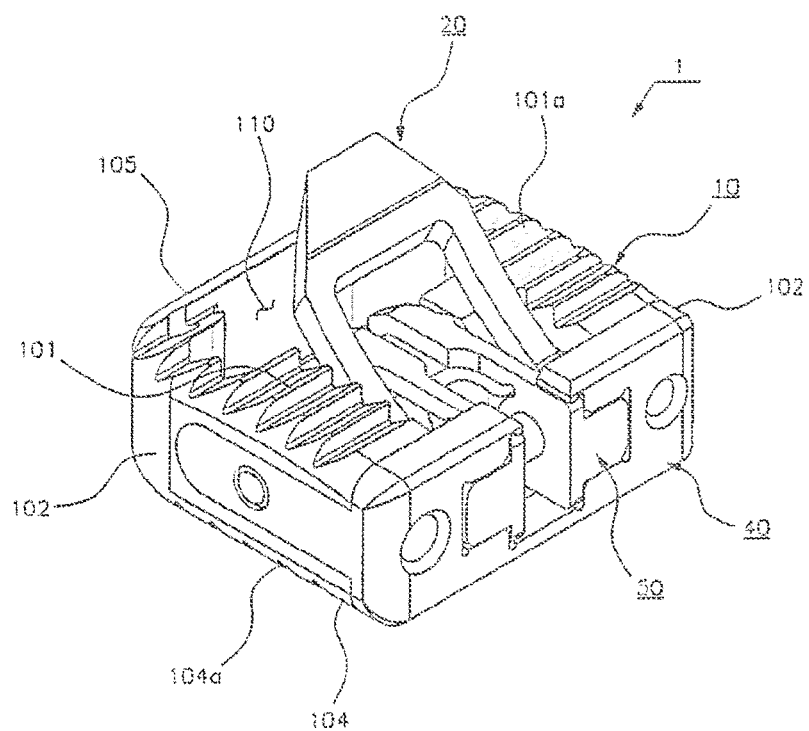
FIG. 1 is a perspective view of a cage in accordance with an embodiment of the present invention.

1: cage 10: main body 101: top surface 02: side surface 103: front surface 104: bottom surface 105: rear surface 110: bone fusion hole 101a, 104a: saw-toothed bodies 120: insertion hole 130: channel part 140: inclined part 141; upper inclined surface 142; top plane surface 143; lower inclined surface 144; bottom plane surface 145; inner wall surfaces 146; protruding surface 151; mounting grooves 152; upper wall 153; lower wall 154: side wall 20: upper spike 21: upper blade 22, 23: arms 24, 25: fastening holes 30: lower spike 31: lower blade 32, 33: arms 34, 35: fastening holes 40: guide block 41: front plate 42: left bar 43: right bar 44: through-hole 45: entrance hole 46: insertion hole 50: clip 51: right retaining jaw 52: left retaining jaw 53: right rib 54: left rib 55: lower rib 56: through-hole 57: base 60: guide block coupling pin 61: clip coupling pin 45 200: insertion mechanism 210: head 211: left head 212: right head 213: upper head 220: first lower support rod 221: push stick guide 230: second lower support rod 240: push stick 241: push plate 242: rod body 243: boss 244: coupling member 250: upper support rod 251: upper support rod guide 252: support body D1: upper vertebral body D2: lower vertebral body

DESCRIPTION OF THE PREFERRED EMBODIMENTS

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

The drawings are provided as examples for communicating the idea of the present invention to those skilled in the art. Thus, the present invention is not limited to the drawings, but may be embodied into other forms.

Furthermore, as long as terms used in this specification are not defined differently, the terms have meanings which are typically understood by those skilled in the art to which the present invention pertains. Moreover, detailed descriptions related to well-known functions or configurations will be ruled out in order not to unnecessarily obscure subject matters of the present invention.

Figure 2:
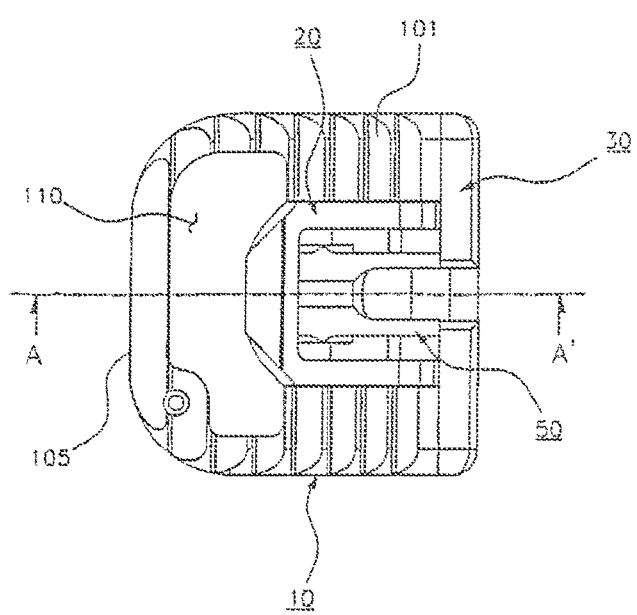
FIG. 2 is a plan view of the cage in accordance with the embodiment of the present invention.
Figure 3:
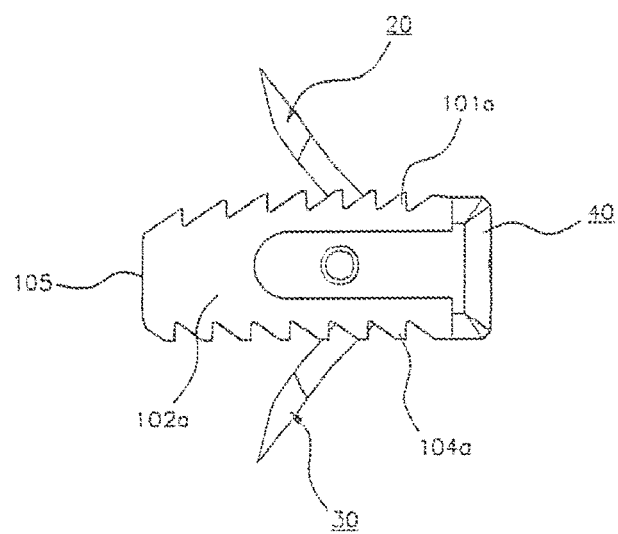
FIG. 3 is a cross-sectional view taken along line A-A' of FIG. 2.

FIG. 1 is a perspective view of a cage in accordance with an embodiment of the present invention. FIG. 2 is a plan view of the cage in accordance with the embodiment of the present invention. FIG. 3 is a cross-sectional view taken along line A-A' of FIG. 2.

Referring to FIGS. 1 to 3, the cage 1 in accordance with the embodiment of the present invention includes a main body 10, a clip 50, upper and lower spikes 20 and 30, and a guide block 40. The clip 50 is inserted into the main body 10. The upper and lower spikes 20 and 30 are coupled to the clip 50 and unfolded to protrude upward and downward through the insertion of the clip 50. The guide block 40 is coupled to the main body 10 so as to guide the insertion of the clip 50.

The upper and lower spikes 20 and 30 unfolded upward and downward from the main body 10 are locked to upper and lower vertebral bodies of a cervical vertebral or spine positioned at the top and bottom of the cage 1 such that the cage 1 is fixed and locked between the vertebral bodies of the cervical vertebral or spine.

The main body 10 of the cage 1 has a hexahedral shape including a top surface 101, both side surfaces 102, a front surface 103, a bottom surface 104, and a rear surface 105. The corners of the main body 10 are rounded.

As illustrated in FIG. 2, the main body 10 has a bone fusion hole 110 formed through the top and bottom surfaces 101 and 104 and a channel part 130 formed therein. The channel part 130 corresponds to a space having an opening through which the clip 50 is inserted into the main body 10 of the cage 1 from the front surface 103.

Furthermore, the main body 10 has an inclined part 140 formed therein. The inclined part 140 guides movement of the upper and lower spikes 20 and 30, when the upper and lower spikes 20 and 30 coupled to the clip 50 inserted through the channel part 130 are unfolded upward and downward. The top of the inclined part 140 is opened so as to unfold the upper and lower spikes 20 and 30 to the outside of the main body 10. The inclined part 140 will be described in more detail.

As illustrated in FIG. 3, the main body 10 has saw-toothed bodies 101a and 104a formed on the top and bottom surfaces 101 and 104 thereof. When the cage 1 is inserted between vertebral bodies of a cervical vertebral or spine, the sawtoothed bodies 10a and 104a improve the contact between the upper and lower vertebral bodies.

Figure 4:
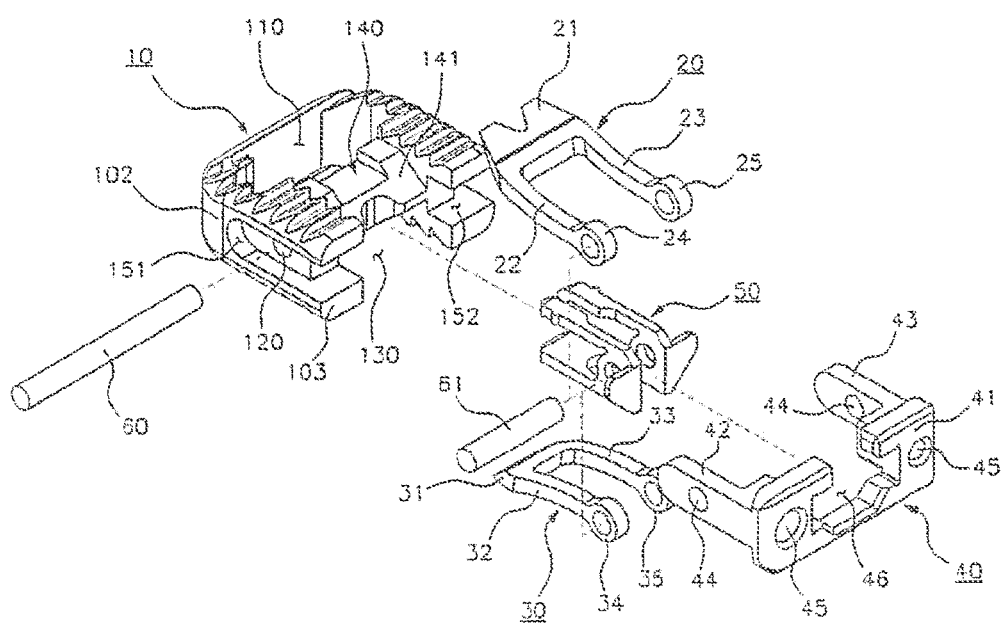
FIG. 4 is an exploded perspective view of the cage in accordance with the embodiment of the present invention.

FIG. 4 is an exploded perspective view of the cage in accordance with the embodiment of the present invention.

As illustrated in FIG. 4, the guide block 40 is coupled to the front surface 103 of the main body 10.

The guide block 40 includes left and right bars 42 and 43 which are formed in the left and right sides thereof and inserted into mounting grooves 151 formed in the left and right side surfaces 102 of the main body 10, respectively, and a guide block coupling pin 61 is passed through throughholes 44 which are formed in the left and right bars 42 and 43 of the guide block 40 and an insertion hole 120 which is vertically formed through the right side surface 102 from the left side surface 102 of the main body 10. Thus, the main body 10 and the guide block 40 are coupled to each other.

After the main body 10 and the guide block 40 are coupled, the clip 50 coupled to the upper and lower spikes 20 and 30 is inserted into the main body 10 through an entrance hole 46 of the guide block 40.

Then, the upper and lower spikes 20 and 30 coupled to the clip 50 are guided along the upper and lower inclined surfaces 141 and 143 of the inclined part 140 formed in the main body 10, and unfolded to protrude upward and downward from the main body 10 while moving upward and downward.

At this time, the upper and lower spikes 20 and 30 are coupled to the clip 50 through the clip coupling pin 60.

Hereafter, the respective elements of the cage 1 in accordance with the embodiment of the present invention will be described in detail.

Figure 5A:
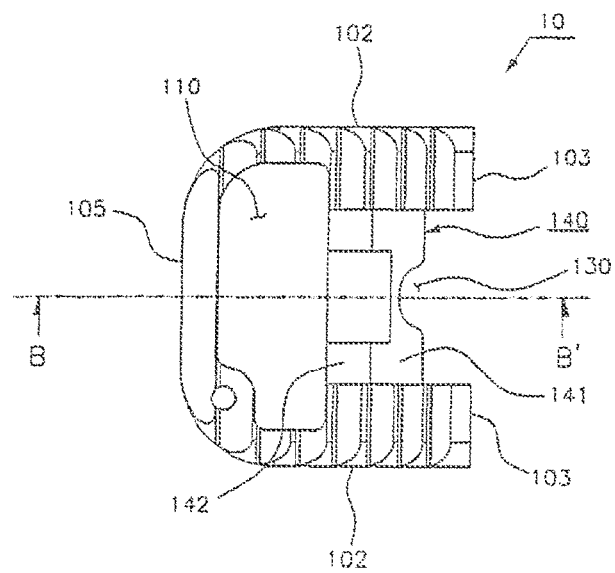
FIGS. 5A to 5D are detailed diagrams of a main body of the cage in accordance with the embodiment of the present invention, FIG. 5C being a cross-sectional view taken along the line B-B' of FIG. 5A.
Figure 5B:
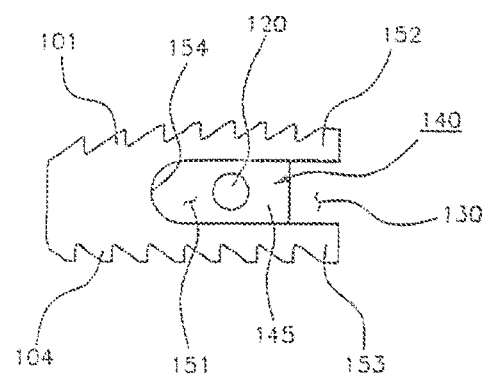
Figure 5C:
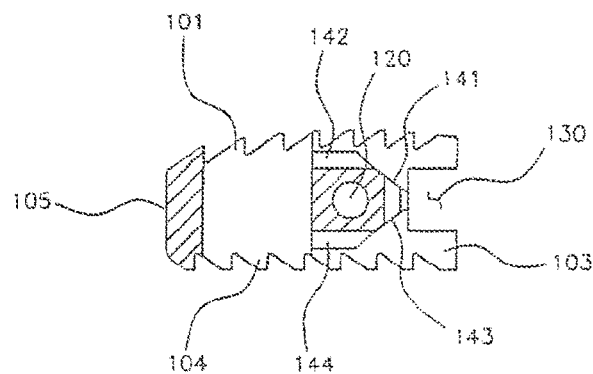
Figure 5D:
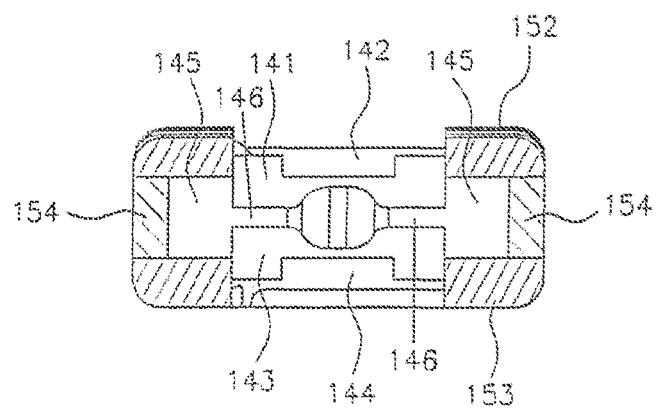

FIGS. 5A to 5D are detailed diagram of the main body of the cage in accordance with the embodiment of the present invention. FIG. 5A is a plan view, FIG. 5B is a side view, FIG. 5C is a cross-sectional view taken along line B-B' of FIG. 5A, and FIG. 5D is a front view.

As described above, the main body 10 of the cage 1 is formed in a hexahedral shape having the top surface 101, both side surfaces 102, the front surface 103, the bottom surface 104, and the rear surface 105, the bone fusion hole 110 is formed through the top and bottom surfaces 101 and 104, and the channel part 130 provides a space such that the clip 50 is inserted from the front surface 103 of the main body 10 and fixed to the central part of the main body 10.

When the upper and lower spikes 20 and 30 coupled to the clip 50 inserted through the channel part 130 are unfolded upward and downward, the inclined part 140 formed in the main body 10 guides the movement of the upper and lower spikes 20 and 30. The top and bottom of the inclined part 140 are opened to unfold the upper and lower spikes 20 and 30 to the outside of the main body 10.

The inclined part 140 has an upper inclined surface 141 formed to guide the upward movement of the upper spike 20, and a top plane surface 142 is formed at an end of the upper inclined surface 141.

Furthermore, the inclined part 140 has a lower inclined surface 143 formed to guide the downward movement of the lower spike 30, and a bottom plane surface 142 is formed at an end of the lower inclined surface 143.

Furthermore, a protruding surface 146 with a predetermined width is formed at the connection between the upper and lower inclined surfaces 141 and 142 of the inclined part 140, and an inner wall surface of a base 57 of the clip 50 is locked to the protruding surface 146 so as to stop the insertion of the clip 50 into the channel part 130.

The inclined part 140 has inner wall surfaces 145 formed at the left and right side surfaces so as to be stepped with respect to the top and bottom surfaces 101 and 104 of the main body 10.

The mounting grooves 151 are formed outside the respective inner wall surfaces 145 such that the left and right bars 42 and 43 of the guide block 40 are mounted in the mounting grooves 151. The mounting groove 151 corresponds to a space formed at the side surface 102 of the main body 10 and includes an upper wall 152, a lower wall 153, and a side wall 154.

The main body 10 of the cage 1 in accordance with the embodiment of the present invention is formed of a metal oz metal alloy such as titanium, zirconium, zirconium oxide, hafnium, platinum, rhodium, niobium, stainless steel for surgery, cobalt chrome (CoCr)-steel, or tantalum or a polymer material such as fiber-reinforced plastic or polyether ether ketone (PEEK). Furthermore, a metal such as aluminum, medical steel, or gold may be added to the metal alloy.

Desirably, PEEK having excellent mechinability and durability may be used as the material of the main body 10.

The bone fuse hole 110 formed in the body 10 may be filled with bone chips extracted from a patient's ilium, for an operation of placing the cage 1. The bone chips stored in the bone fusion hole 110 may grow through the cage as the time passes after the operation, thereby fusing the intervertebral disk of the diseased part to the cervical vertebra or spine.

The insertion hole 120 is formed through the left and right surfaces 102 of the main body 10, in order to fasten the guide block coupling pin 60 for coupling the guide block 40 to the main body 10.

Figure 6A:
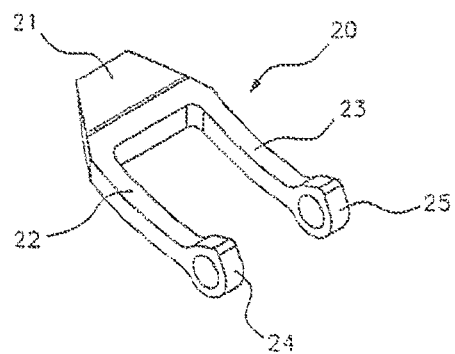
FIGS. 6A to 6C are detailed diagrams of an upper spike of the cage in accordance with the embodiment of the present invention, FIG. 6C being a cross-sectional view taken along the line C-C' of FIG. 6B.
Figure 6B:
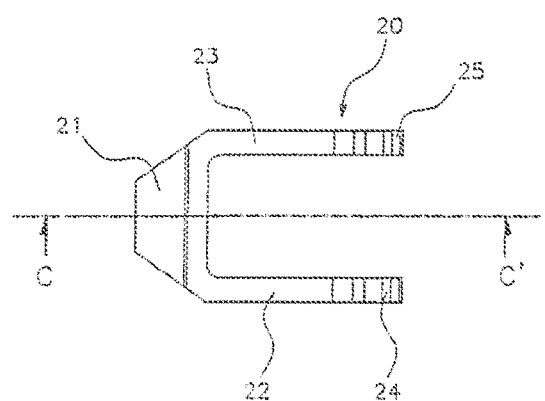
Figure 6C:
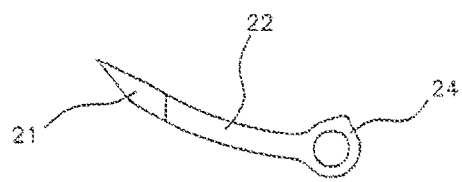
Figure 7A:
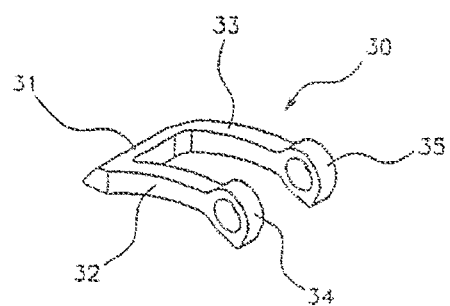
FIGS. 7A to 7C are detailed diagrams of a lower spike of the cage in accordance with the embodiment of the present invention, FIG. 7C being a cross-sectional view taken along the line D-D' of FIG. 5B.
Figure 7B:
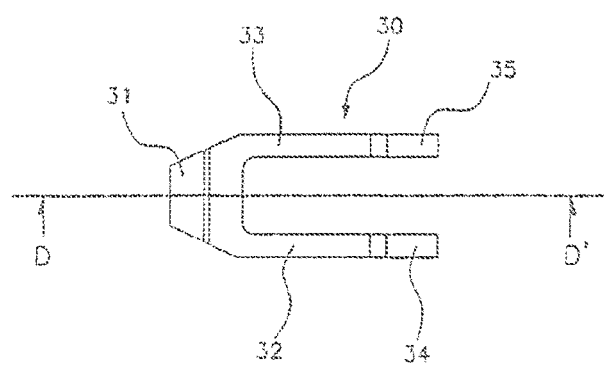
Figure 7C:
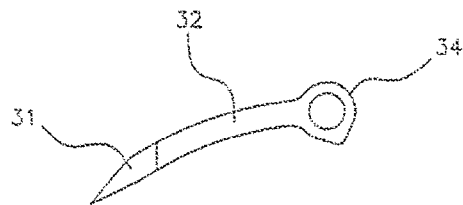
Figure 8A:
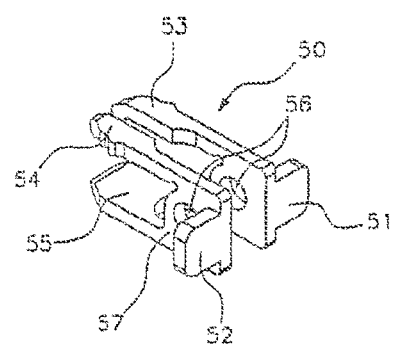
FIGS. 8A to 8D are detailed diagrams of a clip of the cage in accordance with the embodiment of the present invention, FIG. 8C being a cross-sectional view taken along the line E-E' of FIG. B.
Figure 8B:
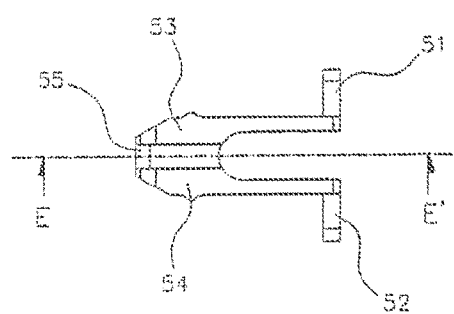
Figure 8C:
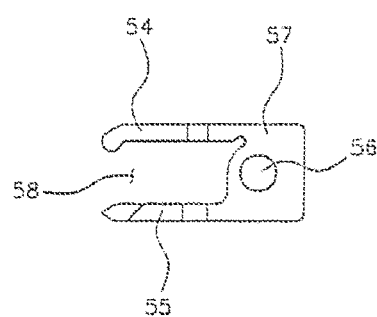
Figure 8D:
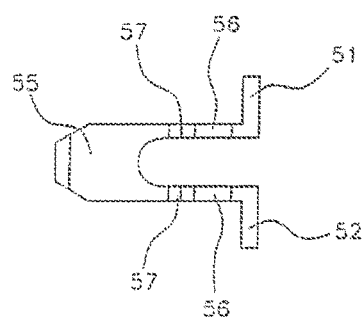

FIGS. 6A to 6C are detailed diagrams of the upper spike of the cage in accordance with the embodiment of the present invention. FIGS. 7A to 7C are detailed diagrams of the lower spike of the cage in accordance with the embodiment of the present invention. FIGS. 8A to 8D are detailed diagrams of the clip of the cage in accordance with the embodiment of the present invention.

Referring to FIG. 6A to 6C, the upper spike 20 coupled to the clip 50 of the cage 1 includes an upper blade 21, arms 22 and 23, and fastening holes 24 and 25. The blade 21 has a pointed end surface formed at an end thereof. The arms 22 and 23 are formed at both sides of the upper blade 21 so as to be extended and inclined downward. The fastening holes 24 and 25 are formed at ends of the respective arms 22 and 23 such that the clip coupling pin 61 for coupling the clip 50 is inserted into the fastening holes 24 and 25.

The upper spike 20 has such a structure that is inclined upward at an increasing angle from the fastening holes 24 and 25. Thus, when the cage 1 in accordance with the embodiment of the present invention is inserted between upper and lower vertebral bodies of a cervical vertebra or spine, the pointed end surface of the upper blade 21 formed at an increasing angle is put into the upper vertebral body and locked to the upper vertebral body such that the cage 1 may be reliably inserted.

Referring to FIGS. 7A to 7C, the lower spike 30 coupled to the clip 50 of the cage 1 includes a lower blade 31, arms 32 and 33, and fastening holes 34 and 35, like the upper spike 20. The lower blade 31 is formed at an end of the lower spike 30 and has a pointed end surface. The arms 32 and 33 are formed at both sides of the lower blade 31 so as to be inclined and extended upward. The fastening holes 34 and 35 are formed at ends of the respective arms 32 and 33 such that a clip coupling pin 61 for coupling the clip 50 is inserted into the fastening holes 34 and 35.

The lower spike 30 has such a structure that is inclined downward at a decreasing angle from the fastening holes 34 and 35. Thus, when the cage 1 in accordance with the embodiment of the present invention is inserted between the upper and lower vertebral bodies of the cervical vertebra or spine, the pointed end surface of the lower blade 31 formed at a decreasing angle is put into the lower vertebral body and locked to the lower vertebral body such that the cage 1 may be reliably inserted with the upper spike 20.

Referring to FIGS. 8a to 8d, the clip 50 for coupling the upper and lower spikes 20 and 30 of the cage 1 includes right and left retaining jaws 51 and 52 and right and left ribs 53 and 54. The right and left retaining jaws 51 and 52 having a plate shape are formed at the front of the base 57 so as to be contacted with an insertion mechanism 200 which serves to push the clip 50 to the inside of the main body 10, and the right and left ribs 53 and 54 are formed at the top rear of the base 57 and extended to be slid and mounted on the top plane surface 142 of the inclined part 140 of the main body 10, when the clip 50 is inserted into the main body 10.

The clip 50 further includes a lower rib 55 formed at the bottom rear thereof and extended to be slid and mounted on the bottom plane surface 144 of the inclined part 140 of the main body 10, when the clip 50 is inserted into the main body 10.

The clip 50 further includes a through-hole 56 formed through the base 57 of the clip 50 so as to fasten the clip coupling pin 61 for coupling the upper and lower spikes 20 and 30.

FIGS. 9 and 10 are diagrams illustrating a state in which the upper and lower spikes of the cage in accordance with the embodiment of the present invention are coupled to the clip.

Figure 9A:
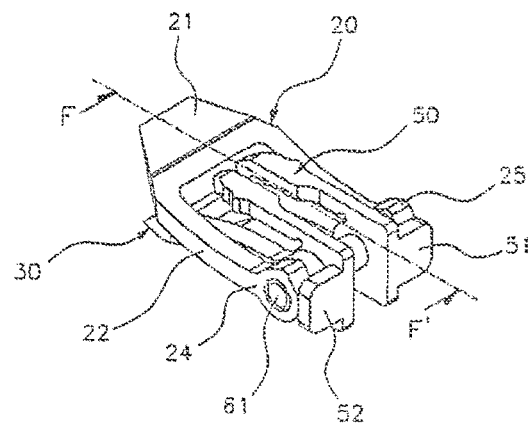
FIG. 9A is a perspective illustrating a state in which upper and lower spikes of the cage, in accordance with the embodiment of the present invention, are coupled to the clip.
Figure 9B:
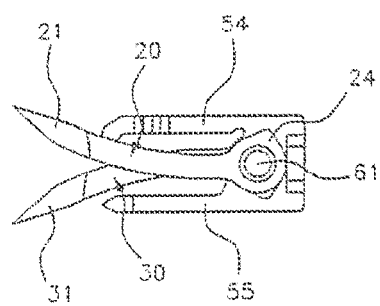
FIG. 9B is a cross-sectional view taken along the line F-F' in FIG. A.

Referring to FIGS. 9A and 9B, the lower spike 30 is positioned inside both arms 22 and 23 of the upper spike 20, and the fastening holes 24 and 25 of the upper spike 20 and the fastening holes 34 and 35 of the lower spike 30 are aligned with each other. In such a state, the fastening holes 24, 25, 34, and 35 of the respective spikes are aligned with the through-holes 56 formed in the base 57 of the clip 50, and the clip coupling pin 61 is then passed through the fastening holes 24, 25, 34, and 35 and the through-holes 56 of the clip 50 so as to couple the upper and lower spikes 20 and 30 to the clip 50.

Figure 10A:
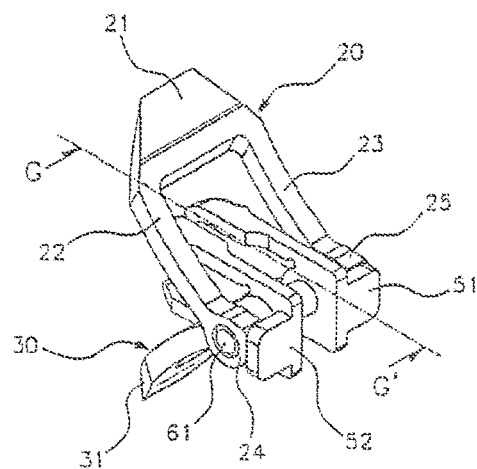
FIG. 10A is another perspective view illustrating a state in which the upper and lower spikes of the cage, in accordance with the embodiment of the present invention, are coupled to the clip, but shown in an alternate position.
Figure 10B:
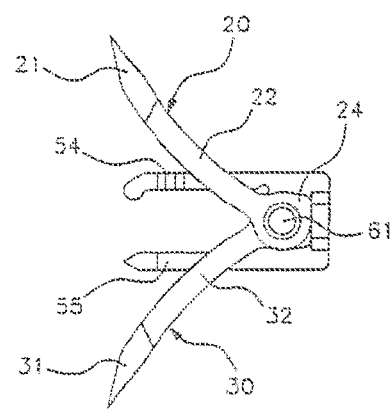
FIG. 10B is a cross-sectional view taken along the line G-G' in FIG. 10A.

Thus, the upper and lower spikes 20 and 30 coupled to the clip 50 are operated as illustrated in FIGS. 10A and 10B. More specifically, the upper blade 21 of the upper spike 20 is revolved upward and downward around the fastening holes 24 and 25 coupled to the clip 50, and the lower blade 31 of the lower spike 20 is revolved upward and downward around the fastening holes 34 and 35.

Figure 11A:
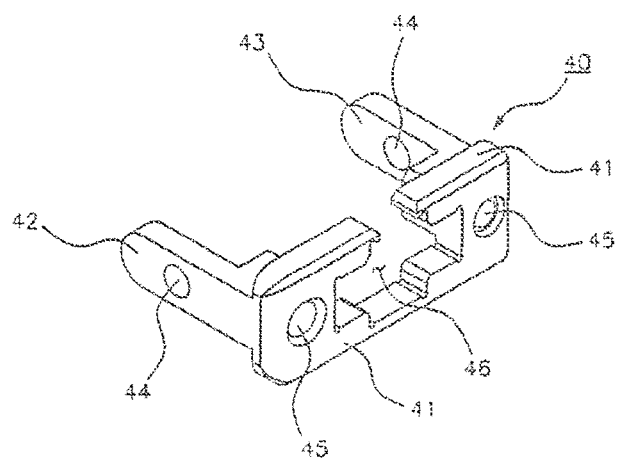
Figure 11B:
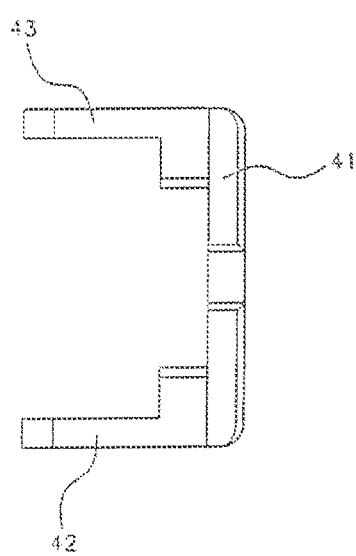
Figure 11C:
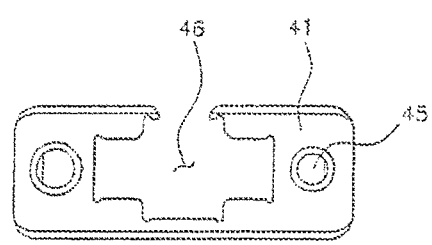

FIGS. 11A to 11C are detailed diagrams of the guide block of the cage in accordance with the embodiment of the present invention. FIG. 11A is a perspective view, FIG. 11B is a plan view, and FIG. 11C is a front view.

Referring to FIGS. 11A to 11C, the guide block 40 in accordance with the embodiment of the present invention is coupled to the main body 10 so as to guide the insertion of the clip 50, and includes a front plate 41, left and right bars 42 and 43, through-holes 44, and an entrance hole 46. The front plate 41 closes the front surface 103 of the main body 10. The left and right bars 42 and 43 are formed to extend from both ends of both side surfaces of the front plate 41 to the rear side. The through-holes 44 are formed through the left and right bars 42 and 43, respectively, such that the guide block coupling pin 60 is inserted into the through-holes 44.

The entrance hole 46 is formed in the center of the front plate 41 so as to provide an opening through which the clip 50 is inserted.

After the left and right bars 42 and 43 of the guide block 40 are inserted into the mounting grooves 151 formed in the left and right side surfaces 102 of the main body 10, the guide block coupling pin 60 is inserted into the through-hole 44 of the left bar 42 and fastened to the through-hole 44 of the right bar 43 through the insertion hole 120. Thus, the main body 10 and the guide block 40 are coupled to each other.

Furthermore, the guide block 40 has one or more insertion holes 45 formed on the front plate 41 thereof such that a coupling screw (not illustrated) fixed to a head 210 of the insertion mechanism 200 to be described below is inserted into the insertion hole 45.

The operation of the case 10 in accordance with the embodiment of the present invention will be described with reference to FIGS. 12A to 12D.

Figure 12A:
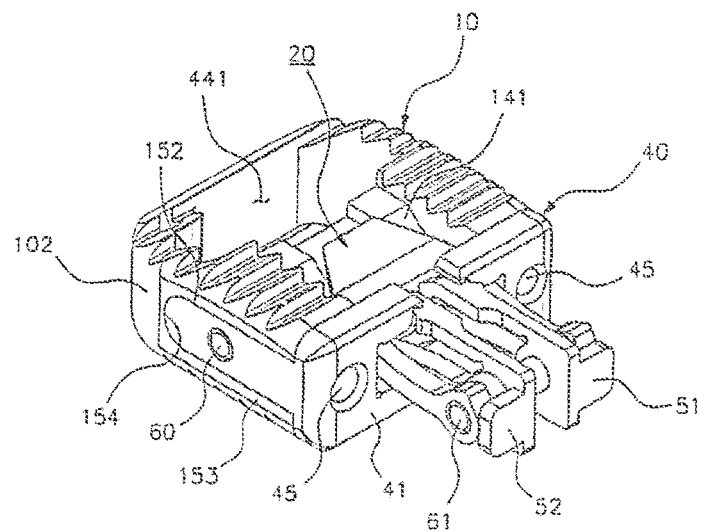
FIG. 12A to 12D are diagrams illustrating the operation state of the cage in accordance with the embodiment of the present invention, FIG. 12C being a cross-sectional view taken along the line H-H' of FIG. 12B.
Figure 12B:
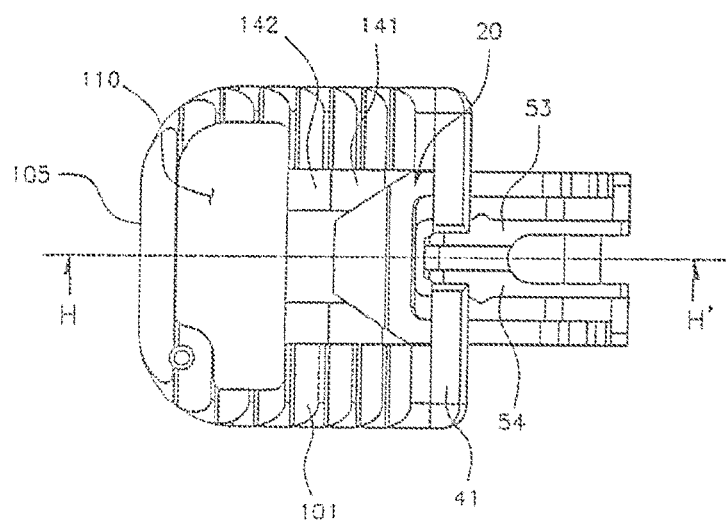
Figure 12C:
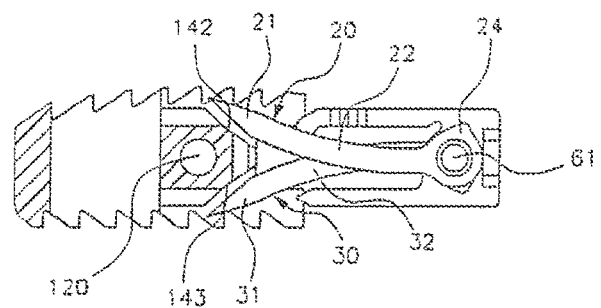
Figure 12D:
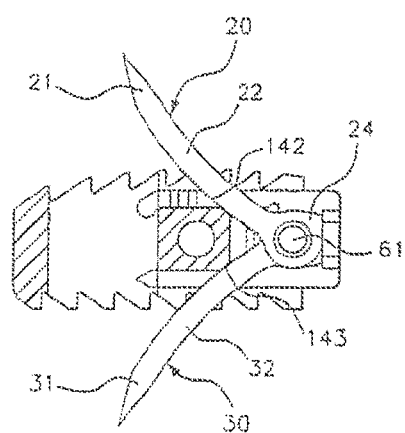

FIG. 12A is a perspective view illustrating that the clip is being inserted, FIG. 12B is a plan view illustrating that the clip is being inserted, FIG. 12C is a cross-sectional view taken along line H-H of FIG. 12B, illustrating that the spikes are folded, and FIG. 12D is a cross-sectional view illustrating that the spikes are unfolded.

The cage 10 in accordance with the embodiment of the present invention is operated in such a manner that the upper and lower spikes 20 and 30 are locked and fixed to upper and lower vertebral bodies of a cervical vertebral or spine at the part from which an intervertebral disc is removed.

First, as illustrated in FIGS. 12A and 12b, the main body 10 and the guide block 40 are coupled to each other, and the right and left retaining jaws 51 and 52 of the clip 50 coupled to the upper and lower spikes 20 and 30 are pushed by the insertion mechanism 200 to be described below. Then, the clip 50 is inserted into the main body 10 through the entrance hole 46 of the guide block 40.

In such a state where the clip 50 is inserted, the upper and lower spikes 20 and 30 are folded so as not to protrude to the outside of the top and bottom surfaces 101 and 104 of the main body 10, while the upper and lower blades 21 and 31 of the upper and lower spikes 20 and 30 reach entrances to the upper and lower inclined surfaces 142 and 143 of the inclined part 140 inside the main body 10, as illustrated in FIG. 12C.

Then, when the clip 50 is further pushed to the inside of the main body 10, the upper and lower spikes 20 and 30 coupled to the clip 50 are unfolded upward and downward as illustrated in FIG. 12D. More specifically, while guided along the upper and lower inclined surfaces 141 and 143 of the inclined part 140 formed in the main body 10, the upper and lower spikes 20 and 30 are moved upward and downward so as to protrude to the outside of the top and bottom surfaces 101 of the main body 10, until the base 57 of the clip 50 is locked to the protruding surface 146 formed in the center of the inclined part 140.

At this time, the right and left ribs 53 and 54 of the clip 50 are slid and mounted on the top plane surface 142 of the inclined part 140, and the lower rib 55 of the clip 50 is slid and mounted on the bottom plane surface 144 of the inclined part 140.

Thus, since the cage 1 in accordance with the embodiment of the present invention includes the upper and lower spikes to perform such an unfolding operation, it is possible to omit a complicated operation of fixing a plate through a screw in a small intervertebral space in the related art. Thus, the convenience of medical treatment and the stability of operation may be improved.

Figure 13A:
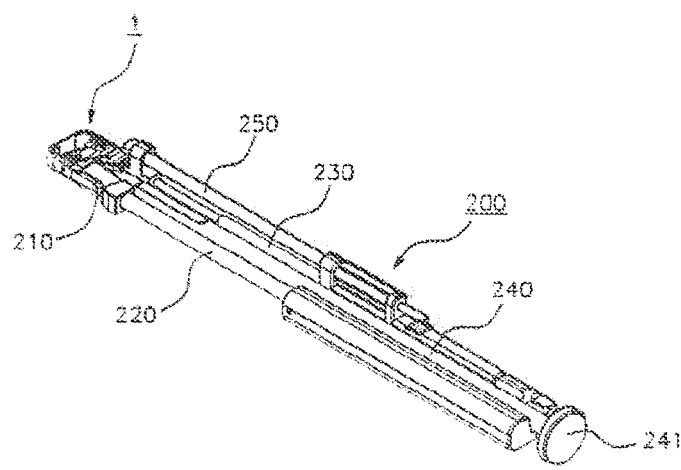
FIGS. 13A to 13D illustrate an insertion mechanism for inserting the cage in accordance with the embodiment of the present invention.
Figure 13B:
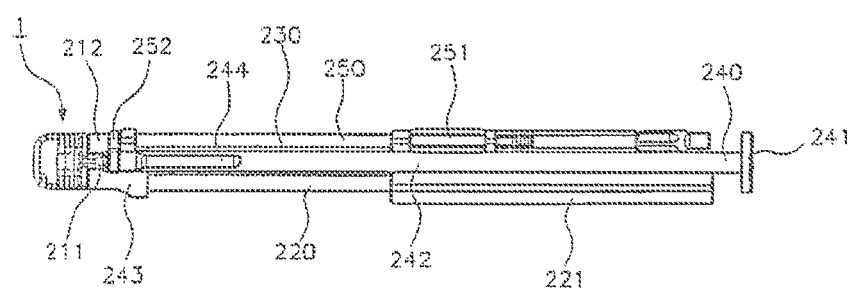
Figure 13C:
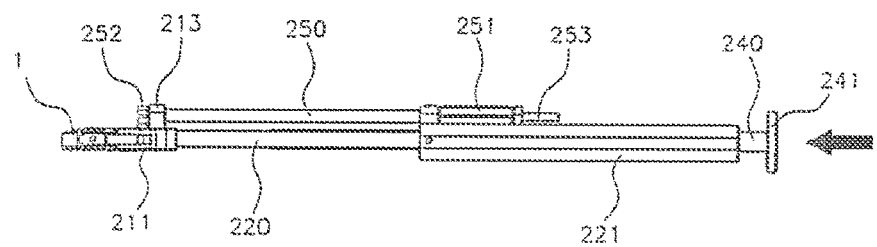

FIGS. 13A to 13C illustrate the insertion mechanism for inserting the cage in accordance with the embodiment of the present invention. FIG. 13A is a perspective view, FIG. 13B is a plan view, and FIG. 13C is a side view illustrating a state in which the spikes are folded.

The insertion mechanism 200 is used to more stably insert the clip 50 coupled to the upper and lower spikes 20 and 30 into the main body 10 of the cage 1.

Referring to FIGS. 13A to 13C, the insertion mechanism 200 for the cage 1 has a head 210 which is coupled to the guide block 40 through a coupling screw (not illustrated) inserted into the insertion hole 45 of the front plate 41 of the guide block 40.

The head 210 is formed in a hexahedral shape, and has a left side coupled to one side of a first lower support rod 220 and a right side coupled to one side of a second lower support rod 230.

Furthermore, a push stick 240 is positioned between the first and second lower support rods 220 and 230. The push stick 240 has a boss 243 formed at one end thereof so as to push the clip 50 into the main body 10.

Figure 13D:
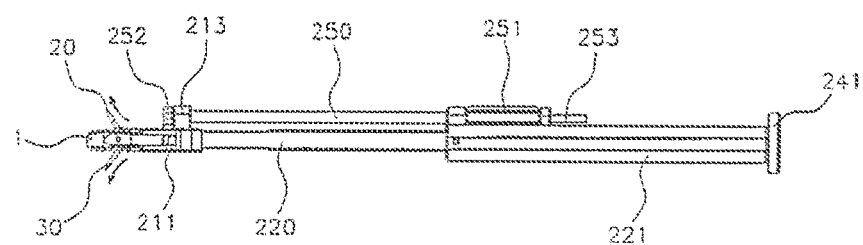

The push stick 240 includes a push plate 241, a rod body 242, and a coupling member 244. The push plate 241 is formed at the other end of the push stick 240, the rod body 242 is extended from the push plate 241, and the coupling member 244 connects the rod body 242 and the boss 243. When the push plate 241 is pushed forward, the boss 243 connected to the coupling member 244 is moved forward through the rod body 242 so as to insert the clip 50 into the main body 10 of the cage 1 as illustrated in FIG. 13D. Then, the upper and lower spikes 20 and 30 are unfolded to protrude to the outside of the top and bottom surfaces of the main body 10.

For such an operation, the head 210 includes a left head 211 coupled to the first lower support rod 220 and a right head 212 coupled to the second lower support rod 230, and the boss 243 of the push stick 240 is fastened between the left and right heads 211 and 212 so as to move forward or backward. The other end of the first lower support rod 220 and the other end of the second lower support rod 240 are inserted into a push stick guide 221 in which the rod body 242 of the push stick 240 is mounted.

The head 210 of the insertion mechanism 200 further includes an upper head 213 into which one end of the upper support rod 250 is inserted, and the other end of the upper support rod 250 is inserted into an upper support rod guide 251 formed at the top of the push guide 221. Furthermore, a support body 252 is attached to the one end of the upper support rod 250.

When the clip 50 is inserted, the upper support rod 250 is contacted with an upper vertebral body of a cervical vertebra or spine, into which the cage 1 is to be placed, thereby improving the stability of the insertion mechanism 200.

Figure 14:
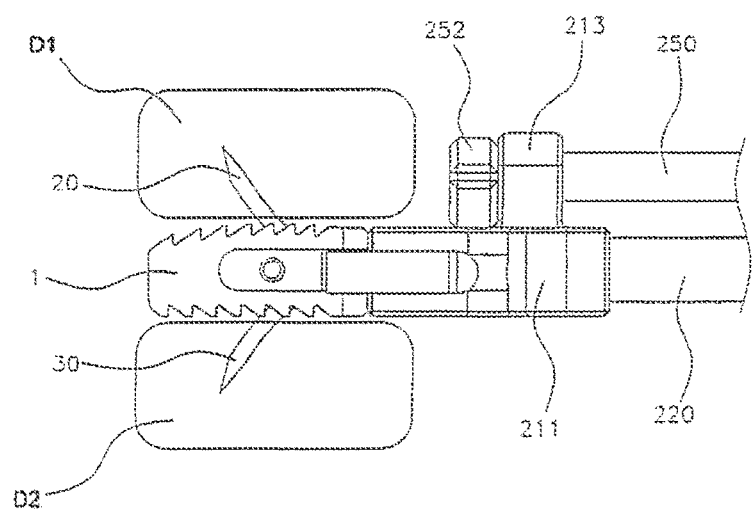
FIG. 14 is a diagram illustrating a state in which the cage in accordance with the embodiment of the present invention is placed.

FIG. 14 is a diagram illustrating a state in which the cage 10 in accordance with the embodiment of the present invention is placed. Referring to FIG. 14, the cage 1 is positioned between upper and lower vertebral bodies D1 and D2 of a cervical vertebra or spine, and the clip 50 is inserted into the main body 10 through the insertion mechanism 200 such that the upper and lower spikes 20 and 30 protrudes to the outside of the top and bottom surfaces 101 and 104 of the main body 10. Then, the pointed end surfaces of the upper and lower blades 21 and 31 at the ends of the spikes 20 and 30 are locked to the upper and lower vertebral bodies D1 and D2 positioned at the top and bottom of the cage 1 such that the cage 1 is fixed and locked between the upper and lower vertebral bodies D1 and D2.

During an actual procedure, the clip 50 is carefully and slowly inserted into the main body 10 while the push plate 241 formed at the other end of the push stick 240 is hit by a hammer for operation (not illustrated).

Thus, the upper and lower spikes 20 and 30 are positioned between the upper and lower vertebral bodies D1 and D2 so as to be reliably fixed to the inner rear sides of the upper and lower vertebral bodies D1 and D2. Thus, it is possible to significantly reduce the possibility that the screw or a part of the plate included in the conventional cages will interfere with the nerve tissue or blood tissue passing through the cervical vertebra or spine at the part from which the intervertebral disk was removed and in which the cage is installed.

While the present invention has been described in connection with the exemplary embodiments illustrated in the drawings, they are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

The invention claimed is:

1. An anchor to secure an intervertebral cage, the anchor comprising:
   a clip adapted to be inserted into a main body of the intervertebral cage through a front face of the intervertebral cage;
   an upper spike pivotably coupled to the clip via a clip coupling pin and unfolded to protrude to an outside of a top surface of the main body through insertion of the clip wherein the upper spike includes a first set of arms extending from an upper blade; and
   a lower spike pivotably coupled to the clip via the clip coupling pin and unfolded to protrude to an outside of a bottom surface of the main body through the insertion of the clip, wherein the lower spike includes a second set of arms extending from a lower blade,
   wherein the first set of arms are disposed outbound of the second set of arms along a longitudinal axis of the clip coupling pin.

2. The anchor of claim 1, wherein the upper spike includes the upper blade comprising an end forming a pointed end surface.

3. The anchor of claim 2, wherein the first set of arms of the upper spike are inclined downward from both sides of the upper blade.

4. The anchor of claim 3, wherein the upper spike includes fastening holes disposed at respective ends of the first set of arms, the fastening holes adapted to receive the clip coupling pin.

5. The anchor of claim 1, wherein the lower spike includes the lower blade comprising an end forming a pointed end surface.

6. The anchor of claim 5, wherein the second set of arms of the lower spike are inclined upward from both sides of the lower blade.

7. The anchor of claim 6, wherein the lower spike includes fastening holes disposed at respective ends of the second set of arms, the fastening holes adapted to receive the clip coupling pin.

8. The anchor of claim 1, wherein each arm of the second set of arms is positioned between the clip and a corresponding arm of the first set of arms.

9. The anchor of claim 1, wherein the clip includes a right retaining jaw and a left retaining jaw, each of the right retaining jaw and the left retaining jaw including a plate shaped and formed at a front of a base.

10. The anchor of claim 9, wherein the clip includes a right rib and a left rib, the right rib and the left rib formed at a rear top of the base.

11. The anchor of claim 10, wherein the right rib and the left rib extend distally from the rear top of the base and are adapted to engage a portion of the intervertebral cage upon insertion of the anchor into the intervertebral cage.

12. The anchor of claim 9, wherein the clip includes through-holes disposed in the base of the clip to receive the clip coupling pin therethrough.

13. The anchor of claim 1, further comprising a guide block coupled to the main body to guide the insertion of the clip into the intervertebral cage by an insertion instrument for implanting the intervertebral cage between vertebral bodies.

14. A bone anchor mechanism comprising:
a clip adapted to be received within an intervertebral implant;
a first spike including a first blade forming a pointed end surface and two first curved arms, each first curved arm terminating in a first pivot hole;
a second spike including a second blade forming a pointed end surface and two second curved arms, each second curved arm terminating in a second pivot hole; and
a coupling pin extending through each pivot hole to pivotably couple the first spike and the second spike to the clip,
wherein each arm of the two second curved arms is located interior to each arm of the two first curved arms.

15. The bone anchor mechanism of claim 14, wherein the two first curved arms are in an opposite direction to the two second curved arms when coupled to the clip with the coupling pin.

16. The bone anchor mechanism of claim 14, wherein each arm of the two second curved arms is positioned between the clip and a corresponding arm of the two first curved arms.

17. The bone anchor mechanism of claim 14, wherein the coupling pin extends through two through-holes in a base portion of the clip.

18. The bone anchor mechanism of claim 17, wherein each first pivot hole and each second pivot hole are disposed on opposite sides of the clip along a length of the coupling pin.

19. The bone anchor mechanism of claim 14, wherein the clip includes a right retaining jaw and a left retaining jaw, each of the right retaining jaw and the left retaining jaw including a plate shape and formed at a front of a base.

* * * * *